US005969148A

United States Patent [19]

[11] Patent Number: 5,969,148

[45] Date of Patent: Oct. 19, 1999

Valente et al.

[54] ONE-POT SYNTHESIS OF PYRAZOLOTRIAZOLE PHOTOGRAPHIC DYE FORMING COLOR COUPLERS AND COUPLER INTERMEDIATES

[75] Inventors: Ronald R. Valente, Rochester; Judith A. Bose, Webster, both of N.Y.

[73] Assignee: Eastman Kodak Company, Rochester, N.Y.

[21] Appl. No.: 09/203,459

[22] Filed: Dec. 2, 1998

[51] Int. Cl.$^6$ .................. C07D 487/04

[52] U.S. Cl. .................. 548/262.4

[58] Field of Search .................. 548/262.4

[56] References Cited

U.S. PATENT DOCUMENTS

| | | |
|---|---|---|
| 5,183,728 | 2/1993 | Romanet et al. . |
| 5,457,210 | 10/1995 | Kim et al. . |
| 5,565,572 | 10/1996 | Potenza et al. . |
| 5,681,691 | 10/1997 | Bose et al. . |

FOREIGN PATENT DOCUMENTS

| | | |
|---|---|---|
| 0 779 543 A1 | 6/1997 | European Pat. Off. . |

*Primary Examiner*—Robert W. Ramsuer
*Attorney, Agent, or Firm*—J. Lanny Tucker

[57] ABSTRACT

Photographic pyrazolotriazole dye forming coupler compounds of coupler intermediate compounds can be readily prepared in a single reaction medium by reacting certain pyrazolotriazole compounds with nitro-substituted aromatic compounds in the presence of a formate salt and a transition metal catalyst. This salt hydrogenates the nitro group and the carbonate by-product induces reaction of the resulting amine with the pyrazolotriazole compound. Yields and purity are high, and reaction time is reduced with the specific set of conditions and reactants, and environmental impact from waste is reduced. In addition, isolation of aromatic amine intermediates is avoided. The resulting pyrazolotriazole compounds can be used themselves as photographic dye forming couplers or further reacted to prepare useful coupler compounds for photographic use.

10 Claims, No Drawings

ONE-POT SYNTHESIS OF PYRAZOLOTRIAZOLE PHOTOGRAPHIC DYE FORMING COLOR COUPLERS AND COUPLER INTERMEDIATES

COPENDING APPLICATION

Reference is made to copending and commonly assigned U.S. Ser. No. 09/204,444 filed on even date herewith by Bose, Valente, Aimino and DeMejo and entitled "Synthesis of Pyrazolotriazole Photographic Dye Forming Color Couplers and Intermediates".

FIELD OF THE INVENTION

This invention relates to a method of preparing pyrazolotriazole compounds that are useful as photographic dye forming couplers or as intermediates for the preparation of pyrazolotriazole photographic dye forming coupler compounds. In particular, it relates to a method of preparing certain 1-H-pyrazolo[5,1-c]-1,2,4-triazole compounds in a single-reaction medium. This invention is useful in the photographic industry.

BACKGROUND OF THE INVENTION

Color photographic silver halide materials are used to provide color images with the use of certain dye forming compounds that are usually in the various photosensitive silver halide layers of the materials. These dye forming compounds are conventionally known as "dye forming couplers" and are reactive with suitable oxidized forms of color developing agents used during photoprocessing to provide the desired dye images. Since most of such silver halide materials (such as color negative films and color papers) provide images based on what is known in the art as "subtractive color mixing", they typically include dye forming couplers that will provide cyan, yellow and magenta dyes in the appropriate photosensitive layers.

Pyrazolotriazoles have been known to be useful magenta dye forming couplers for some time, and various processes are known for preparing them, all of which usually include various chemical reactions taken in specific order. Such processes add functionality that defines the desired dye forming coupler early in the synthesis. These processes result in the lack of generality of the process and the need to make different intermediates for different dye forming coupler end products.

It is well known in the art [for example, U.S. Pat. No. 5,183,728 (Romanet et al), U.S. Pat. No. 5,457,210 (Kim et al) and U.S. Pat. No. 5,565,572 (Potenza et al)] that compounds defined by Formula IV below are known to be photographic dye forming couplers, as well as precursors to other photographic dye forming couplers.

It is known from EP 779,543 (Bose et al) that one common synthetic route to these types of compounds involves the high pressure catalytic reduction of a nitro aromatic compound (shown as Formula II below) using hydrogen to form an aromatic amine of Formula III, and then reaction of the aromatic amine with a compound of Formula IV under basic conditions. This is generally a two step process involving the isolation and handling of the aromatic amine of Formula III.

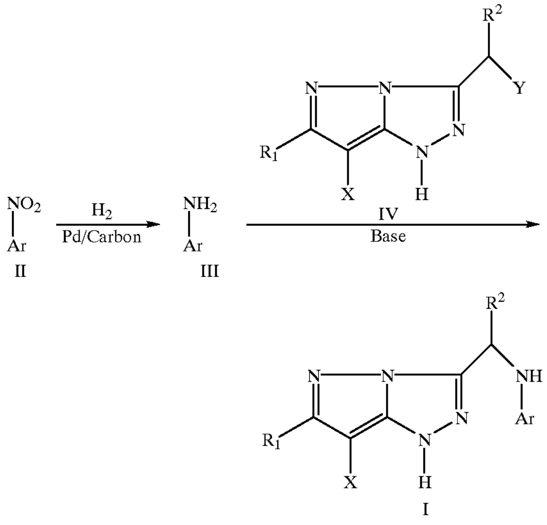

There are several disadvantages to such a two-step process. It includes increased cycle time due to increased handling requirements, increased air emissions if drying of the intermediate is required, and increased total volume of solvent needed. In addition, with this particular synthetic route, two different types of reaction vessels are needed. The catalytic hydrogenation of the first step requires specially designed high pressure equipment, while the displacement second reaction can be carried out in a standard reaction vessel. Additionally, this method requires the use of highly flammable hydrogen gas that presents a critical safety issue.

It is a desire in the industry to identify a chemical process that would transform aromatic nitro compounds of Formula II and the compounds of Formula IV into coupler precursors or couplers of Formula I in one step using one reaction vessel. It is also desired to accomplish this task with high chemical yield, high purity, short cycle time, low solvent usage, increased safety and minimal negative environmental impact.

One possible alternative to catalytic hydrogenation is a hydrogen transfer reaction [as described for example by Johnstone, et. al, *Chem. Rev.,* 1985, 85, 129, Entistle, et. al, *J. Chem. Soc., Perkin I,* 1977, 443, and U.S. Pat. No. 5,041,605 (Huson et al)]. There are many possible hydrogen sources that can be used but each results in a different by-product.

Thus, there remains a need for an improved, single reaction medium synthesis of pyrazolotriazole dye forming coupler intermediates.

SUMMARY OF THE INVENTION

These problems are overcome with a method for preparing a pyrazolotriazole dye forming coupler compound or coupler intermediate compound of Structure I in a single reaction medium, the method comprising reacting a nitro-substituted aromatic compound $NO_2$—Ar with a compound of Structure IV in the presence of a formate salt,

I

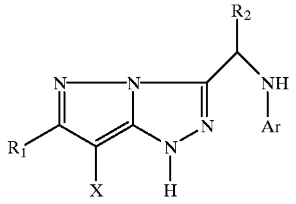

IV

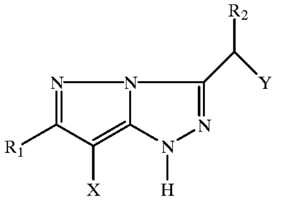

wherein Ar is an aromatic group (as defined below), $R_1$ is an alkyl, aryl, alkoxy, aryloxy or amido group, $R_2$ is hydrogen or an alkyl or aryl group, X is hydrogen or a coupling-off group or a precursor thereof, and Y is a leaving group that is capable of being replaced by an elimination-addition reaction, whereby the nitro-substituted aromatic compound is converted to the corresponding aromatic amine that is then, without isolation from the single reaction medium, reacted with the compound of Structure IV.

This invention also provides a method for preparing a pyrazolotriazole dye forming coupler compound comprising:

A) forming a compound of Structure I as described above, and

B) further reacting the compound of Structure I obtained in step A.

The present invention is advantageous because it provides a dye forming coupler compound or coupler intermediate compound in high yield and purity using a synthesis that can be carried out in a single reaction medium using a nitro-substituted aromatic compound. In addition, the method of this invention is safer since the use of highly flammable hydrogen is avoided, and the impact upon the environment is minimized because less solvent is used and there are less by- products for disposal.

These advantages are achieved by the use of formate salts as the hydrogen donor in conversion of the nitro-substituted aromatic compound. The by-products from use of the formate salt in the first step are carbonate and bicarbonate salts that are very effective at promoting the second step, the displacement reaction to form a Structure I compound. It is therefore possible to run these two steps sequentially, in one reaction vessel, with no isolation of the intermediate aromatic amine. The combination of the hydrogen transfer reaction and the displacement reaction into one step was a surprising result because most other hydrogen transfer donors do not yield basic by-products that will promote the displacement reaction.

The present invention can be used to prepare pyrazolotriazole dye forming color couplers that are reactive with oxidized photographic color developing agents to provide photographic dyes. Such coupler compounds may be useful in various photographic silver halide materials, or in photochemical processing solutions that are useful for providing colored images from such materials. Alternatively, the compounds prepared using the present invention may be further reacted as one skilled in the art would readily understand, to add ballast groups, coupling off groups or other reactive groups. The resulting compounds can then be used in any suitable manner.

DETAILED DESCRIPTION OF THE INVENTION

The present invention is a method for converting nitro-substituted aromatic compounds of Structure II to aromatic amines of Structure III and then to coupler intermediates of Structure I by reaction with compounds of Structure IV in a single reaction medium that includes a formate salt. The two reactions in the single step process are generally carried out using the conditions described below. Upon completion of the second reaction, the resulting salts can be removed by filtration or by adding a water-immiscible organic solvent and washing with water or a mildly acidic solution. Any organic solvent remaining in reaction medium can be removed by distillation.

The general reaction scheme of the invention is shown as follows:

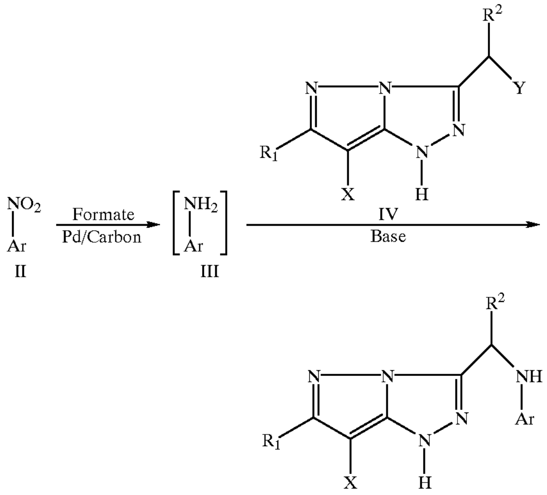

Ar is any suitable carbocyclic or heterocyclic aromatic group having from 6 to 14 carbon, nitrogen, oxygen or sulfur atoms in the ring structure, and one or more substituents (up to 4, defined below) on the aromatic ring that do not interfere with the reactions or end use of the coupler intermediates or dye forming couplers.

In Structure IV, $R_1$ can be, but is not limited to, any of the groups conventionally found in this position on corresponding photographic dye forming couplers or precursors thereof. For example, useful $R_1$ groups include, but are not limited to, substituted or unsubstituted alkyl having from 1 to 12 carbon atoms (for example, methyl, ethyl, methoxymethyl, isopropyl, t-butyl, n-pentyl, n-hexyl, decyl, dodecyl, benzyl and phenethyl), substituted or unsubstituted cycloalkyl having 5 to 12 carbon atoms in the ring (or combination of rings, such as cyclopenyl, cyclohexyl and 4-methylcyclohexyl), substituted or unsubstituted alkoxy having 1 to 12 carbon atoms (such as methoxy, 2-ethoxy, isopropoxy, methoxymethoxy and benzoxy), substituted or unsubstituted alkyloxysulfonyl (wherein the alkyl portion has 1 to 12 carbon atoms as defined above), substituted or unsubstituted alkylsulfonyl (wherein the alkyl portion has 1 to 12 carbon atoms as defined above), substituted or unsubstituted aryl having 6 to 12 carbon atoms in the aromatic ring (or combination of rings, such as phenyl, p-methylphenyl, 3-methoxyphenyl, naphthyl, tolyl, halophenyl groups, nitrophenyl groups, aminophenyl groups, carboxyphenyl groups, methoxycarbonylphenyl groups, hydroxyphenyl groups and ethoxyphenyl groups), substituted or unsubstituted aryloxy having 6 to 12 carbon atoms in the aromatic ring (or combination of rings, such as phenoxy, p-methylphenoxy, halophenoxy groups, aminophenoxy groups and alkylphenoxy groups), substituted or unsubstituted aryloxysulfonyl wherein the aryl portion is as defined above, and substituted or unsubstituted arylsulfonyl wherein the aryl portion is as defined above.

$R_1$ can also be an acyl group (such as acetyl or $—OCOCH_2CH_3$), substituted or unsubstituted amino (such as substituted or unsubstituted alkyl and arylamines), amido (such as methamido, 2-ethylamido and t-butylamido), substituted or unsubstituted alkylthio wherein the alkyl portion has 1 to 12 carbon atoms (as defined above), substituted or unsubstituted arylthio wherein the aryl portion has from 6 to 12 carbon atoms in the ring structure (as defined above), or a substituted or unsubstituted heterocyclyl having from 5 to 12 carbon, nitrogen, oxygen or sulfur atoms in the heterocyclic ring (or combination of rings). Useful heterocyclyl groups include, but are not limited to, pyridyl, pyrimidyl, pyrazolyl, pyrrolyl, oxazoyl, thiazolyl, furanyl and thiophenyl.

In preferred embodiments, $R_1$ is a substituted or unsubstituted alkyl, substituted or unsubstituted aryl, amido, substituted or unsubstituted acyl, substituted or unsubstituted alkoxy or substituted or unsubstituted aryloxy group as defined above (such as methyl, ethyl, isopropyl, t-butyl, methoxy, ethoxy, phenyl, phenoxy, a methylphenyl group, a chlorophenyl group, a nitrophenyl group, a methoxyphenyl group and t-butylamido). Amido and acyl are the least preferred of such groups. Most preferably, $R_1$ is a substituted or unsubstituted alkyl group, such as substituted or unsubstituted methyl, ethyl, isopropyl and t- butyl groups, or a phenyl or phenoxy group.

$R_2$ is hydrogen, or a substituted or unsubstituted alkyl, substituted or unsubstituted aryl or substituted or unsubstituted heterocyclyl group, as defined above for $R_1$ (obviously, $R_1$ and $R_2$ can be different groups). Preferably, $R_2$ is a substituted or unsubstituted aryl group (such as phenyl, chlorophenyl groups, methylphenyl groups, methoxyphenyl groups, nitrophenyl groups) or a substituted or unsubstituted alkyl group having 1 to 4 carbon atoms (such as methyl, ethyl, isopropyl, isobutyl and t-butyl groups). More preferably, $R_2$ is a substituted or unsubstituted phenyl group (for example, m- or p-nitrophenyl) or substituted or unsubstituted alkyl group (for example, a methyl, ethyl or t-butyl group). Unsubstituted phenyl and methyl are the most preferred $R_2$ groups.

Also within Structure IV, X is hydrogen or a coupling off group or a precursor thereof. Such coupling off groups are well known in the photographic art as groups that can be replaced by oxidized color developing agent during photographic processing (that is, color development). Such groups can determine the chemical equivalency of a coupler, that is whether it is a 2-equivalent or a 4-equivalent coupler, or modify the reactivity of the coupler. The presence of hydrogen at the coupling site ("X") provides a 4-equivalent coupler, and the presence of the coupling off group usually provides a 2-equivalent coupler.

Representative coupling off groups (or precursors thereof) include, but are not limited to, halo (such as chloro or bromo), substituted or unsubstituted alkoxy having 1 to 12 carbon atoms (as defined above for $R_1$), substituted or unsubstituted aryloxy having 6 to 12 carbon atoms in the aromatic ring (or combination of rings, as defined above for $R_1$), substituted or unsubstituted hetero-oxy (that is a heterocyclyl attached through an oxy group) having from 5 carbon and heteroatoms in the heterocyclyl ring(s), substituted or unsubstituted alkylthio wherein the alkyl portion has from 1 to 12 carbon atoms as defined above for $R_1$, arylthio wherein the aryl portion has from 6 to 12 carbon atoms as defined above for $R_1$, heterocyclyl as defined above for $R_1$, sulfonyloxy, acyloxy, acyl, sulfonamido, mercaptopropionic acid, phosphonyloxy and arylazo.

Preferably, X is hydrogen, halo, phenoxy, a substituted or unsubstituted alkylthio group (such as methylthio or carboethoxyethylthio) or a substituted or unsubstituted arylthio group (such as phenylthio). Most preferably, X is hydrogen, chloro, phenoxy or carboethoxyethylthio.

Y is a leaving group that is capable of being replaced in an elimination-addition reaction. Such groups include, but are not limited to, halo, hydroxy, substituted or unsubstituted alkoxy having 1 to 12 carbon atoms (as defined above for $R_1$), substituted or unsubstituted aryloxy having 6 to 12 carbon atoms in the aryl portion (as defined above for $R_1$), substituted or unsubstituted acyloxy (such as acetoxy and $—OCOalkyl_{C2-C8}$), substituted or unsubstituted alkylsulfonyloxy or arylsulfonyloxy (as defined above for $R_1$). Preferred Y groups include, but are not limited to, halo, and substituted or unsubstituted aryloxy, acyloxy and alkoxy groups. More preferably, Y is halo (such as chloro), substituted phenoxy (such as p-nitrophenoxy) or an acetoxy group. Addition-elimination reactions are described for coupler synthesis in U.S. Pat. No. 5,183,728 (noted above).

Unless otherwise specifically stated, substituent groups that may be substituted on compounds of Structures I–IV described herein include any groups, whether substituted or unsubstituted, that do not destroy properties necessary for photographic utility. When the term "group" is applied to the identification of a substituent containing a substitutable hydrogen, it is intended to encompass not only the substituent's unsubstituted form, but also its form that is further substituted with any group or groups as herein mentioned. Suitably, the group may be halo or may be bonded to the remainder of the molecule by an atom of carbon, silicon, oxygen, nitrogen, phosphorous, or sulfur. The substituent may be, for example, halo (such as chloro, bromo or fluoro), nitro, hydroxyl, cyano, carboxyl, or groups which may be further substituted, such as alkyl, including straight or branched chain alkyl [such as methyl, trifluoromethyl, ethyl, t-butyl, 3-(2,4-di-t-pentylphenoxy) propyl, and tetradecyl], alkenyl (such as ethylene and 2-butene), alkoxy [such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy and 2-dodecyloxyethoxy], aryl (such as phenyl, 4-t-butylphenyl, 2,4,6-trimethylphenyl and naphthyl), aryloxy (such as phenoxy, 2-methylphenoxy, α- or β-naphthyloxy and 4-tolyloxy), carbonamido [such as acetamido, benzamido, butyramido and tetradecanamido, α-(2,4-di-t-pentyl-phenoxy)acetamido, α-(2,4-di-t-pentylphenoxy)butyramido, α-(3-pentadecylphenoxy)-hexanamido and α-(4-hydroxy-3-t-butylphenoxy)-tetradecanamido], 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t- butylphenoxycarbonylamino, phenylcarbonylamino, 2,5-(di-t-pentylphenyl)carbonylamino, p-dodecyl-phenylcarbonylamino, p-toluylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-toluylureido, N-(m-hexadecylphenyl)ureido, N,N-(2,5-di-t-pentylphenyl)-N'-ethylureido, and t-butylcarbonamido, sulfonamido (such as methylsulfonamido, benzenesulfonamido, p-toluylsulfonamido, p-dodecylbenzenesulfonamido, N-methyltetradecylsulfonamido, N,N-dipropyl-sulfamoylamino and hexadecylsulfonamido), sulfamoyl {such as N-methylsulfamoyl, N-ethylsulfamoyl, N,N-dipropylsulfamoyl, N-hexadecylsulfamoyl and N,N-dimethylsulfamoyl), N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl}, carbamoyl {such as N-methylcarbamoyl, N,N-dibutylcarbamoyl, N-octadecylcarbamoyl, N-[4-(2,4-di-t-pentylphenoxy) butyl]carbamoyl, N-methyl-N-tetradecylcarbamoyl, and N,N-dioctylcarbamoyl}, acyl [such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl], sulfonyl (such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl and p-toluylsulfonyl), sulfonyloxy (such as dodecylsulfonyloxy and hexadecylsulfonyloxy), sulfinyl (such as methylsulfinyl, octylsulfinyl, 2-ethylhexylsulfinyl, dodecylsulfinyl, hexadecylsulfinyl, phenylsulfinyl, 4-nonylphenylsulfinyl and p-toluylsulfinyl), thio [such as ethylthio, octylthio, benzylthio, tetradecylthio, 2-(2,4-di-t-pentylphenoxy) ethylthio, phenylthio, 2-butoxy-5-t-octylphenylthio and p-tolylthio], acyloxy (such as acetyloxy, benzoyloxy, octadecanoyloxy, p-dodecylamidobenzoyloxy, N-phenylcarbamoyloxy, N-ethylcarbamoyloxy, and cyclohexylcarbonyloxy), amine (such as phenylanilino, 2-chloroanilino, diethylamine or dodecylamine), imino [such as 1-(N-phenylimido)ethyl, N-succinimido or 3-benzylhydantoinyl], phosphate (such as dimethylphosphate and ethylbutylphosphate), phosphite (such as diethyl and dihexylphosphite), a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl, quaternary ammonium, such as triethylammonium, and silyloxy (such as trimethylsilyloxy).

If desired, the substituents may themselves be further substituted one or more times with one or more of the described substituent groups. The particular substituents used may be selected by those skilled in the art to attain the desired photographic properties for a specific application and can include, for example, hydrophobic groups, solubilizing groups, blocking groups, releasing or releasable groups, etc. Generally, the above groups and substituents thereof may include those having up to 48 carbon atoms, typically 1 to 36 carbon atoms and usually less than 24 carbon atoms, but greater numbers are possible depending on the particular substituents selected.

Some representative compounds of Structure IV are listed in TABLE I below:

TABLE I

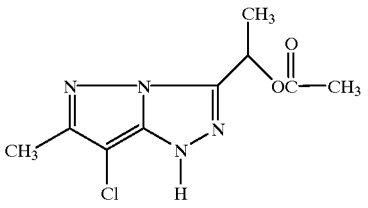

CP-1

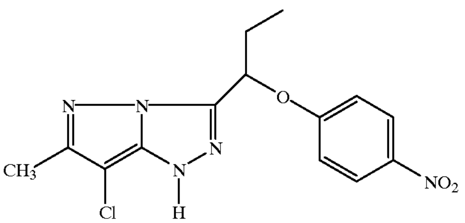

CP-2

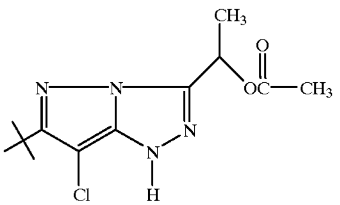

CP-3

TABLE I-continued
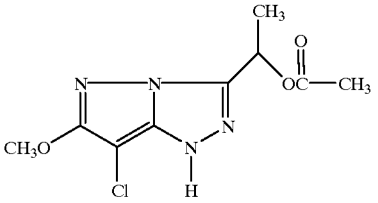
CP-4
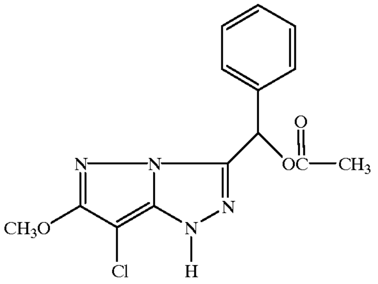
CP-5
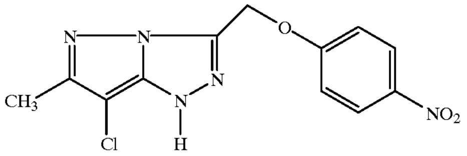
CP-6
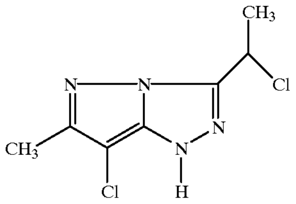
CP-7
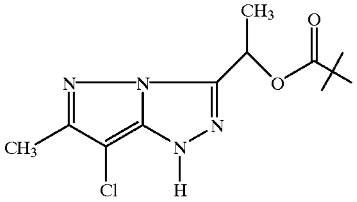
CP-8
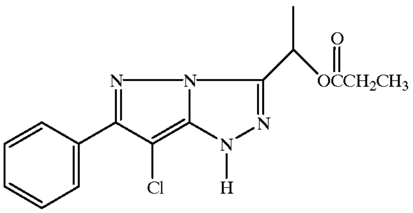
CP-9
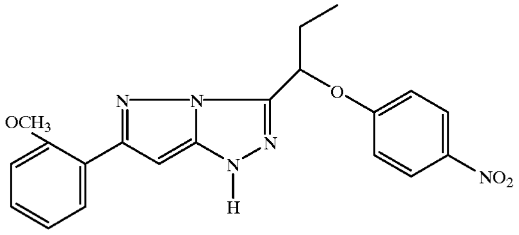
CP-10

TABLE I-continued
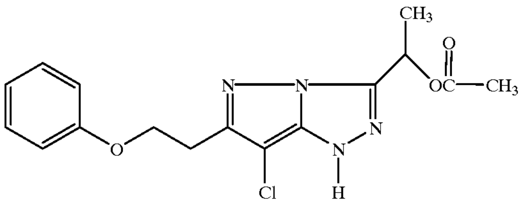
CP-11
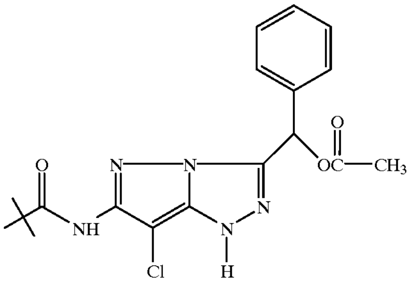
CP-12
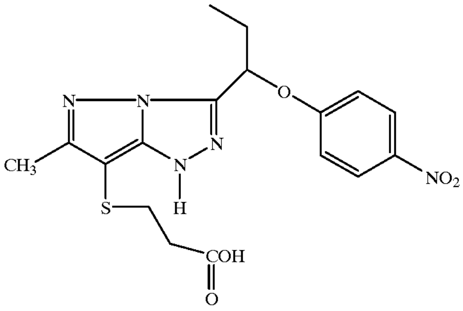
CP-13
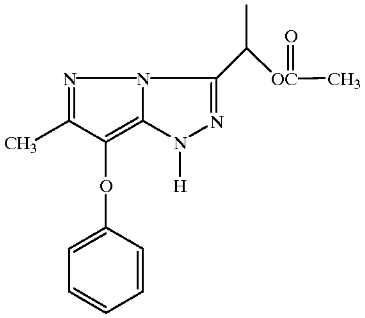
CP-14
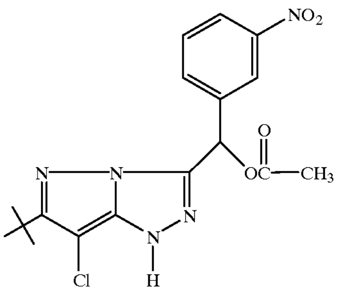
CP-15

TABLE I-continued

CP-16

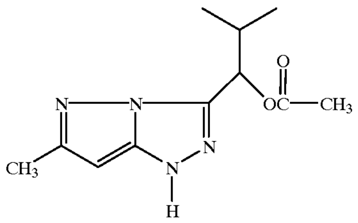

CP-17

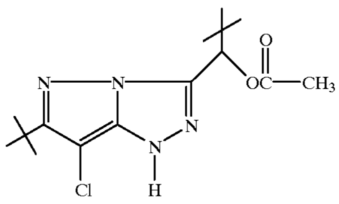

CP-18

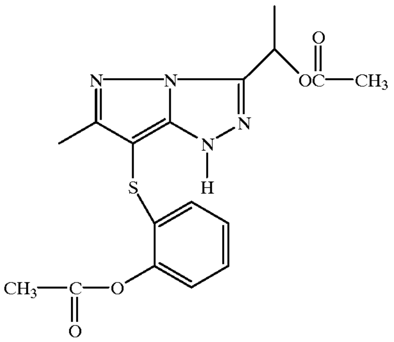

The compounds represented by Structure IV can be provided for the practice of this invention by preparing them from conventional starting materials and using known reaction conditions (for example, as described in the Potenza et al and Kim et al patents noted above).

Aromatic amines of Structure III used in the practice of the invention are formed during the process from various aromatic (Ar) carbocyclic or heterocyclyl groups that have a nitro group and up to 4 other substituents (Structure II). Useful aromatic compounds include, but are not limited to, substituted or unsubstituted phenyl, naphthyl, anthryl, pyridinyl, pyridazinyl, triazinyl and isoquinolinyl groups. If there are two or more substituents on the aromatic ring (other than the nitro group), they can be combined to form a fused ring with the aromatic ring system.

Particularly useful Ar groups include phenyl or other 6- to 10-membered carbocyclic aryl groups having large ballast groups as a substituent. Such ballast groups generally have at least 12 carbon, oxygen, sulfur and nitrogen atoms in the chain.

Useful Ar groups include those defined as aryl groups for $R_1$. Representative aryl groups include, but are not limited to, phenyl, alkylphenyl groups, bromophenyl groups, carboxyphenyl groups, cyanophenyl groups, acetylphenyl groups, alkoxyphenyl groups, and others that would be readily apparent to one skilled in the art. The preferred aryl groups are substituted and unsubstituted phenyl groups. Useful aromatic heterocyclyl groups have 5 to 12 carbon, nitrogen, oxygen or sulfur atoms in the aromatic ring (or combination of rings) as described above. Representative aromatic heterocyclyl groups include, but are not limited to, pyridinyl and isoquinolinyl.

Useful nitro-substituted aromatic compounds of Structure II can generally be obtained from a number of commercial sources including Aldrich Chemical Co., or prepared using conventional starting materials and reaction conditions (see for example, EP-A-0 779,543 noted above).

Some typical reactants of Structure II are listed below in TABLE II.

NAS-1

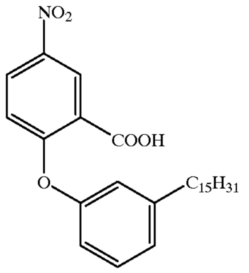

NAS-2

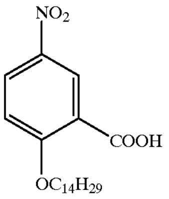

-continued

NAS-3

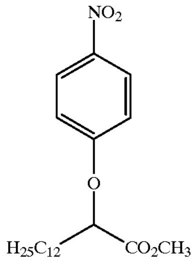

NAS-4

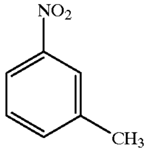

NAS-5

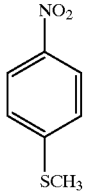

NAS-6

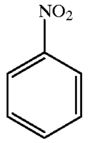

NAS-7

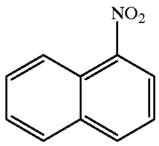

NAS-8

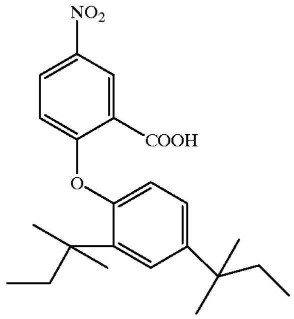

NAS-9

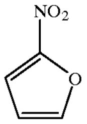

NAS-10

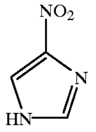

-continued

NAS-11

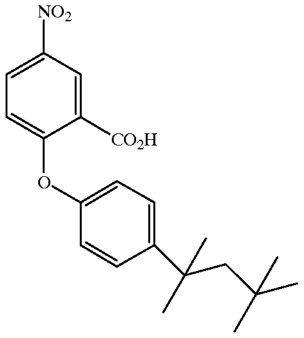

NAS-12

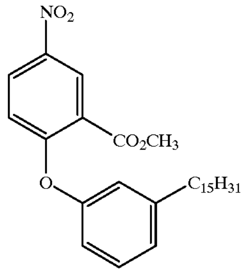

NAS-13

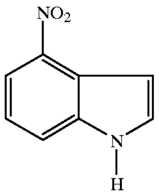

NAS-14

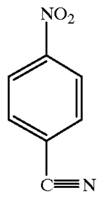

NAS-15

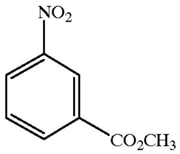

NAS-16

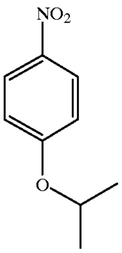

As noted above, the pyrazolotriazole compounds prepared using the present invention can be used as photographic dye forming coupler compounds without further modification. Alternatively, they can be used as "intermediates" that are further reacted to provide the desired photographic dye forming coupler compounds of interest. Examples of compounds of Structure I obtained using the method of this invention are listed below in TABLE III.
TABLE III
P-1
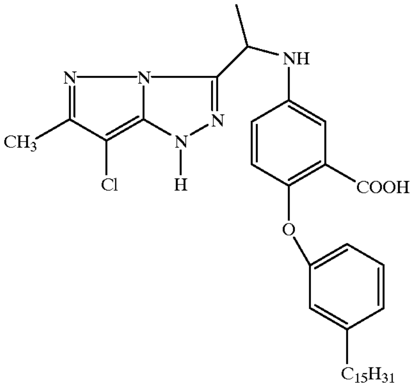
P-2
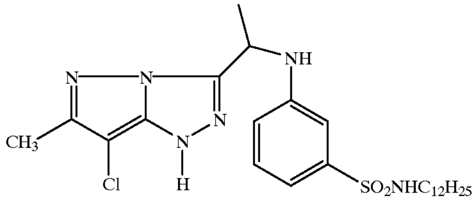
P-3
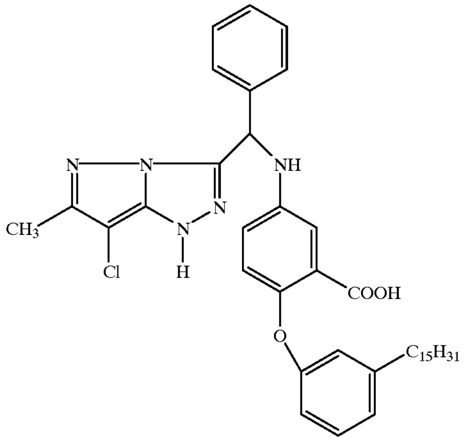
P-4
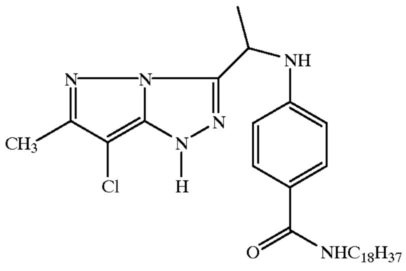
TABLE III-continued
P-5
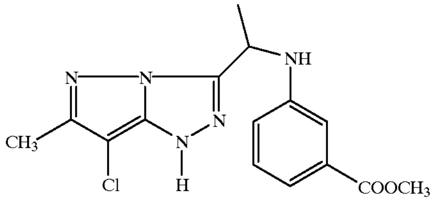
P-6
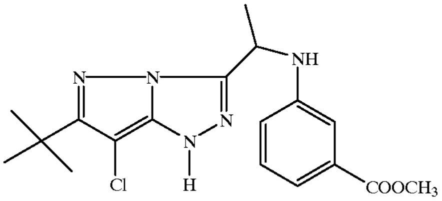
P-7
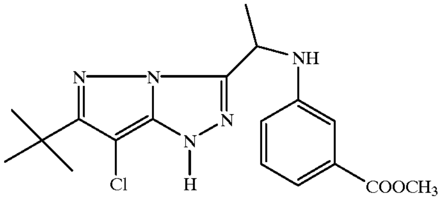
P-8
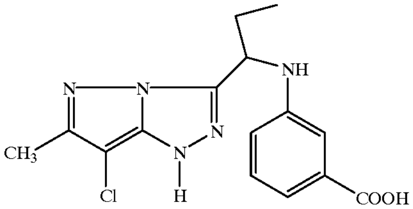
P-9
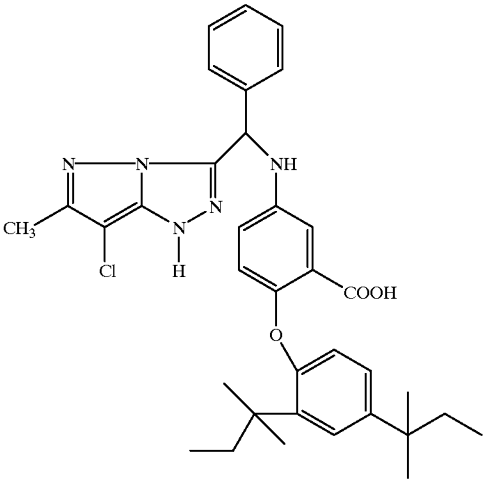
P-10
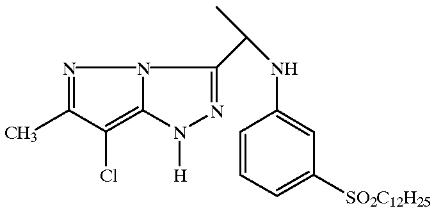

TABLE III-continued

P-11

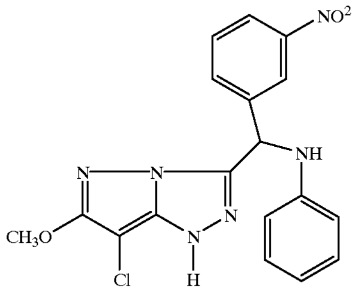

P-12

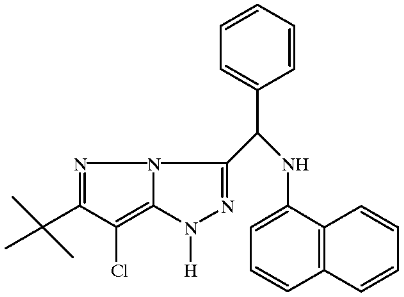

P-13

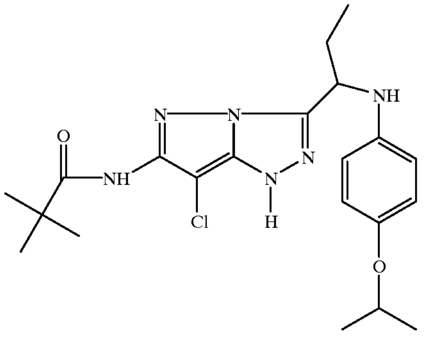

P-14

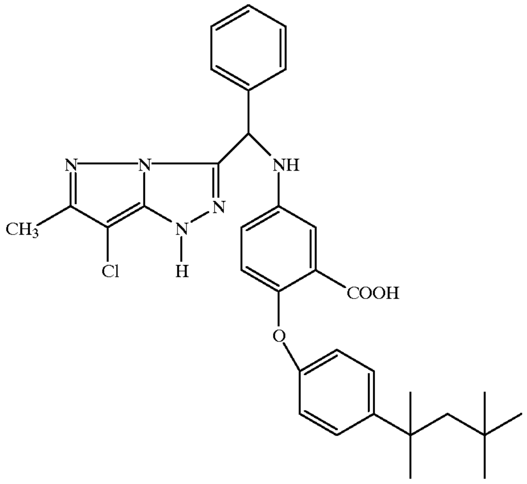

TABLE III-continued

P-15

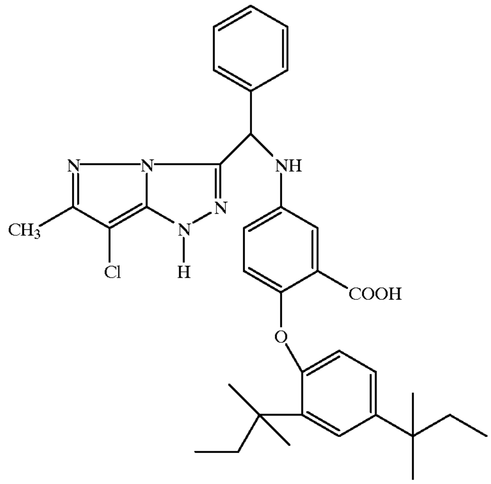

The general conditions for preparing the compounds of Structure I include a reaction temperature that is at least 25° C., preferably at least 35° C., and more preferably at least 40° C. The reaction temperature can be generally up to 65° C., preferably up to 55° C., and more preferably up to 50° C.

The reaction media can be aqueous, or composed of one or more organic polar solvents, or a mixture of water and one or more of such solvents. Useful polar organic solvents include, but are not limited to, alcohols (such as isopropanol), alkyl acetates (such as ethyl acetate and propyl acetate), tetrahydrofuran and acetonitrile. Particularly useful polar organic solvents include isopropanol, ethyl acetate, propyl acetate, or mixtures or two or more of these. Isopropanol is most preferred.

Within the reaction mixture is one or more formate salts that include the alkali metal, ammonium and trialkylammonium salts (wherein the alkyl portions of the cations have from 1 to 4 carbon atoms). The ammonium, sodium and potassium salts are most preferred.

The amount of formate salt in the reaction medium is generally at least 3 molar equivalents, preferably at least 3.5 molar equivalents, based on the concentration of the reactants of Structure IV in the medium. The amount can be generally up to 6 molar equivalents, and preferably up to 4.5 molar equivalents, based on the concentration of the reactants of Structure IV in the reaction medium.

It is essential to include a transition metal catalyst in the reaction medium in order to promote the conversion of the nitro-substituted aromatic compound to the corresponding amine. Useful transition metal catalysts are well known in the art and include, for example, palladium (on carbon), platinum and others that would be readily apparent to one skilled in the art. The catalysts can also be removed by filtration at the end of the method.

The compounds of Structures II and IV are generally present initially in the reaction mixture at a 1:1 stoichiometric ratio, although a higher amount of one or the other reactant can also be used if desired.

If the compounds of Structure I are to be further reacted to provide useful photographic dye forming coupler compounds, various known reactions can be used, including but not limited to, acylation (reaction with an acid chloride), sulfonylation (reaction with a sulfonyl chloride), or isocyanation (reaction with an isocyanate) in suitable positions on the molecules. Details of some useful reactions are provided, for example, in U.S. Pat. No. 5,565,572 (noted above) and EP-A-0 779,543 (noted above), both incorporated herein by reference with regard to such reaction methods.

The following examples illustrate the practice of this invention which is not to be limited thereby.

EXAMPLE 1

Comparative Reactions to Form Intermediates

TABLE IV below shows the results for carrying out the noted reaction using the present invention compared to two known processes. Included in TABLE IV are the hydrogen source for the first reaction, whether the resulting amine was isolated, total solvent volume for both steps, total reaction time for both steps (does not include isolation time for Control A), and the % isolated "Yield" of the resulting product intermediate P-1.

The individual synthetic procedures are as follows:

Invention: To a stirred solution of Compound NAS-1 (5.0 g, 10.6 mmol) in a mixture of 25 ml of tetrahydrofuran and 25 ml of isopropanol were added ammonium formate (2.69 g, 42.6 mmol) and 10% palladium (Pd) on carbon catalyst (0.5 g, 50% wet). The reaction mixture was heated to 45° C. for 2 hours. Thin layer chromatography (TLC, 1:1 ethyl acetate:heptane) showed the reaction was complete. Compound CP-1 (2.57 g, 10.6 mmol) was then added, and the reaction mixture was allowed to stir an additional 4 hours. It was then cooled to room temperature and partitioned between 250 ml of propyl acetate and 250 ml of 5% HCl. The organic layer was dried over magnesium sulfate and concentrated to an oil. The product was purified by column chromatography on silica using a solvent gradient of 1:4 ethyl acetate:heptane up to 2:3 ethyl acetate:heptane to give 5.58 g of an off-white solid. High pressure liquid chromagraphy (HPLC) showed the material to be 86.6% pure. The material was further purified by recrystallization from ethyl acetate:heptane 1:7 to afford 4.15 g of Compound P-1 as a white solid (63% yield).

Control A: A solution of Compound NAS-1 (5.0 g, 10.6 mmol) in a mixture of 25 ml of tetrahydrofuran and 25 ml of isopropanol was treated with 10% palladium on carbon catalyst (0.5 g, 50% wet). This mixture was placed on a Parr hydrogenator under 50 psi (3.5 kg-force/$cm^2$) of hydrogen. After 2.5 hours, the reaction mixture was removed. TLC (1:1 ethyl acetate:heptane) showed the reaction was complete. The catalyst was removed by filtration through a CELITE™ pad that was then washed with a mixture of the organic solvents. The filtrate was concentrated under reduced pressure to give an oil that was then dissolved in tetrahydrofuran (50 ml). Compound CP-1 (2.57 g, 10.6 mmol) and triethylamine (1.47 mL, 10.6 mmol) were added. The reaction mixture was heated to reflux for 5 hours, cooled to room temperature, and partitioned between 250 ml of propyl acetate and 250 ml of 5% HCl. The organic layer was dried over magnesium sulfate and concentrated to dark oil. The product was purified by chromatography on silica with a solvent gradient of 1:4 ethyl acetate:heptane up to 1:1 ethyl acetate:heptane to give 5.12 g of an off-white solid. This material was further purified by recrystallization from ethyl acetate:heptane 1:7 to afford 3.69 g of Compound P-1 as a white solid (56% yield).

Control B: To a stirred solution of Compound NAS-1 (5.0 g, 10.6 mmol) in a mixture of 25 ml of tetrahydrofuran and 25 ml of isopropanol under a nitrogen atmosphere was added 10% palladium on carbon catalyst (0.5 g, 50% wet). The reaction mixture was heated to 55° C., and hypophosphorous acid (5.6 ml, 42.6 mmol, 50% aqueous solution) was added dropwise over 5 minutes. TLC after 4 hours showed that starting material remained so an additional 0.2 g of catalyst and 2.8 ml of hypophosphorous acid were added. After an additional 2.5 hours, TLC showed the reaction forming the aromatic amine was complete. Compound CP-1 (2.57 g, 10.6 mmol) was then added, and the reaction mixture was allowed to stir an additional 14 hours at 55° C. The reaction mixture was cooled to room temperature, and the solvents were removed under reduced pressure. The resulting residue was partitioned between 250 ml of propyl acetate and 250 ml of water. The layers were separated and the organic layer was washed with brine and concentrated. The resulting mixture was purified by chromatography on silica with a solvent gradient of 1:4 ethyl acetate:heptane up to 100% ethyl acetate. The major product that was isolated required a second chromatography to purify. The isolate product was identified as the amine intermediate (1.9 g, 41% yield), not the desired Compound P-1.

It can be seen from TABLE IV that the present invention provided a 63% yield of desired product without isolation of the intermediate aromatic amine. Somewhat lower yield was obtained for Control A, but the method required isolation of the aromatic amine, considerably lengthening the process. Control B shows the use of hypophosphorous acid as the hydrogen donor in the first step, and no isolation of the aromatic amine. However, no reaction occurred to produce the desired product, but about 41% of the aromatic amine was isolated at the end of the method. Obviously, the phosphoric acid by-product from hypophosphorous acid did not promote reaction of the aromatic amine with the compound of Structure IV. Thus, not every known hydrogen transfer source will provide by-products that will then promote the formation of compounds of Structure I in a single reaction medium.

TABLE IV

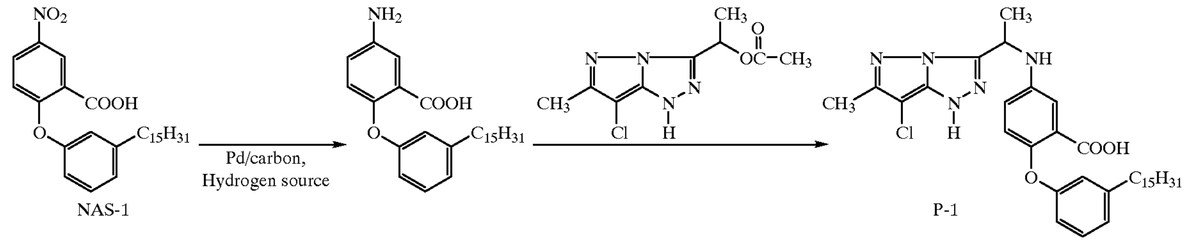

NAS-1

P-1

| Reaction | Hydrogen Source | Isolation of amine | Total solvent volume | Total reaction time | Yield |
|---|---|---|---|---|---|
| Example 1 | $(NH_4)^+HCOO^-$ | No | 50 ml | 6 hours | 63% |
| Control A | $H_2$ | Yes | 100 ml | 7.5 hours | 56% |
| Control B | $H_3PO_2$ | No | 50 ml | 17 hours | 0% |

In the following examples of the invention, all compounds were characterized by spectral methods including mass spectroscopy and NMR. HPLC analysis was used to determine the purity of the isolated compounds as well as to monitor the progress of the reactions.

EXAMPLE 2

Preparation of Compound P-1

To a stirred mixture of Compound NAS-1 (47.0 g, 0.10 mol) in ethyl acetate (300 ml) and isopropanol (60 ml) was added ammonium formate (25.2 g, 0.40 mol) followed by 5% palladium on carbon catalyst (dry) (2.0 g). The reaction mixture was warmed to 45° C. for 2 hours. TLC (45:30:1 toluene:dioxane:acetic acid) showed the reaction was not complete. An additional 1 g of catalyst was added and the reaction was heated to 50° C. until all of the starting material was consumed. The reaction was cooled to room temperature and Compound CP-1 (24.3 g, 0.10 mol) was added. The resulting reaction mixture was warmed to 40° C. overnight. TLC showed some aniline intermediate remained, but all of Compound CP-1 had been consumed. An additional 2.4 g of Compound CP-1 was added and the reaction was stirred at 40° C. for 2 hours. The reaction mixture was then cooled to room temperature, washed with 5% HCl and then washed with brine. The organic layer was dried over magnesium sulfate, and concentrated under reduced pressure. The product was purified by crystallization from ethyl acetate:heptane (1:7) to yield 48 g (77%) of Compound P-1.

EXAMPLE 3

Preparation of Compound P-3

To a stirred mixture of Compound NAS-1 (24.0 g, 0.05 mol) in ethyl acetate (150 ml) and isopropanol (35 ml) was added ammonium formate (12.5 g, 0.20 mol) followed by 5% palladium on carbon catalyst (dry) (1.0 g). The reaction mixture was warmed to 50° C. for 3 hours. TLC (system 12) showed that the reaction was not complete. An additional 1.0 g of catalyst was added and the reaction was heated to 50° C. overnight. The reaction mixture was cooled to room temperature and Compound CP-5 (15.3 g, 0.05 mol) was added. The reaction mixture was then warmed to 40° C. overnight. TLC (ethyl acetate) showed that some aniline intermediate remained, but all of Compound CP-5 had been consumed. An additional 1.5 g of Compound CP-5 was added and the reaction was stirred at 40° C. for 2 hours. The reaction mixture was then cooled to room temperature, washed with 5% HCl followed by washing with brine. The organic layer was dried over magnesium sulfate, and concentrated under reduced pressure. The product was purified by recrystallization from ethyl acetate/acetonitrile to give 24.8 g (73%) of Compound P-3 as a yellow solid.

EXAMPLE 4

Preparation of Compound P-9

To a stirred mixture of Compound NAS-8 (39.9 g, 0.10 mol) in ethyl acetate (200 ml) and isopropanol (50 ml) was added ammonium formate (27.7 g, 0.44 mol) followed by 5% palladium on carbon catalyst (dry) (2.0 g). The reaction mixture was warmed to 50° C. overnight. TLC showed that the reaction to form the aniline intermediate was complete. Compound CP-5 (30.5 g, 0.10 mol) was then added, and the reaction mixture was stirred at 50° C. for 4 hours. The reaction mixture was partitioned between 1.0 molar HCl (200 ml) and ethyl acetate (50 ml). The organic layer was dried over magnesium sulfate, and concentrated under reduced pressure. The product was purified by slow crystallization from acetonitrile to provide 45.4 g (74.1%) of Compound P-9.

EXAMPLE 5

Preparation of Compound P-14

To a stirred mixture of Compound NAS-1 (10.0 g, 0.027 mol) in tetrahydrofuran (40 ml) and isopropanol (25 ml) was added ammonium formate (7.5 g, 0.118 mol) followed by 5% palladium on carbon catalyst (dry) (0.4 g). The reaction mixture was warmed to 40° C. for 3.5 hours. TLC showed that the reaction to form the aniline intermediate was complete. Compound CP-1 (6.8 g, 0.028 mol) was then added, and the reaction mixture was stirred at 40° C. for 4 hours. The reaction mixture was partitioned 1.0 molar HCl (100 ml) and ethyl acetate (50 ml). The organic layer was dried over magnesium sulfate, and concentrated under reduced pressure. The product was purified by slow crystallization from acetonitrile (70 ml) to provide 54.2 g (61%) of Compound P-14.

EXAMPLE 6

Preparation of Compound P-15

To a stirred mixture of Compound NAS-8 (25.78 g, 0.065 mol) in ethyl acetate (125 ml) and isopropanol (25 ml) was added ammonium formate (16.3 g, 0.26 mol) followed by 5% palladium on carbon catalyst (dry) (1.0 g). The reaction mixture was warmed to 40° C. for 3.5 hours. TLC (system 12) showed that the reaction to form the aniline intermediate was complete. Compound CP-1 (14.6 g, 0.060 mol) was then added, and the reaction mixture was stirred at 40° C. for 4 hours. It was then partitioned between 1.0 molar HCl (200 ml) and ethyl acetate (50 ml). The organic layer was dried over magnesium sulfate, and concentrated under reduced pressure. The product was purified by slow crystallization from acetonitrile to provide 24.7 g (74.7%) of Compound P-15.

EXAMPLE 7

Preparation of Compound P-16

To a stirred mixture of Compound NAS-11 (43.5 g, 0.12 mol) in ethyl acetate (250 ml) and isopropanol (60 ml) was added ammonium formate (29.5 g, 0.47 mol) followed by 5% palladium on carbon catalyst (3.5 g, 50% wet). The reaction mixture was warmed to 45° C. overnight. TLC showed that the reaction to form the aniline intermediate was complete. Compound CP-5 (36.6 g, 0.12 mol) was then added and the reaction mixture was stirred at 40° C. for 6 hours. It was then was partitioned between 1.0 molar HCl (100 ml) and ethyl acetate (50 ml). The organic layer was dried over magnesium sulfate, and concentrated under reduced pressure. The product was purified by slow crystallization from acetonitrile to provide 43.3 g (62%) of Compound P-16.

The invention has been described in detail with particular reference to certain preferred embodiments thereof, but it will be understood that variations and modifications can be effected within the spirit and scope of the invention.

We claim:

1. A method for preparing a pyrazolotriazole dye forming coupler compound or coupler intermediate compound of Structure I in a single reaction medium containing a transition metal catalyst, said method comprising reacting a nitro-substituted aromatic compound $NO_2$—Ar with a compound of Structure IV in the presence of a formatic salt

I

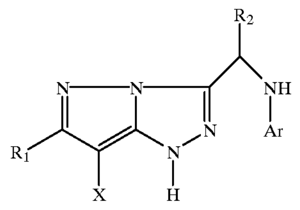

IV

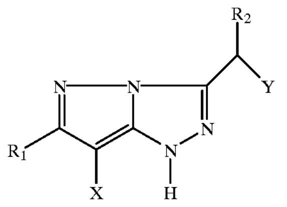

wherein Ar is an aromatic group, $R_1$ is an alkyl, aryl, alkoxy, aryloxy, acyl or amido group, $R_2$ is hydrogen or an alkyl or aryl group, X is hydrogen or a coupling-off group or a precursor thereof, and Y is a leaving group that is capable of being replaced in an elimination-addition reaction, whereby said nitro-substituted aromatic compound is converted to the corresponding aromatic amine that is then without isolation from said single reaction medium, reacted with said compound of Structure IV.

2. The method of claim 1 carried out at a temperature of from about 20 to about 65° C.

3. The method of claim 1 wherein said nitro-substituted aromatic compound is a nitro-substituted phenyl, naphthyl, anthryl, pyridinyl, pyridazinyl, triazinyl, or isoquinolinyl group having a nitro group and up to 4 other substituents on the aromatic ring.

4. The method of claim 3 wherein said nitro-substituted aromatic compound is a nitro-substituted phenyl group.

5. The method of claim 1 wherein said nitro-substituted aromatic compound is

NAS-1

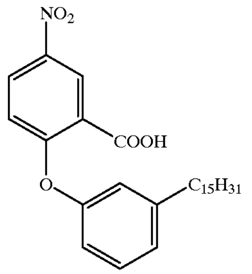

NAS-2

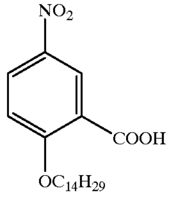

NAS-3

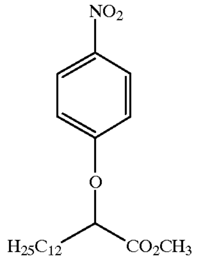

NAS-4

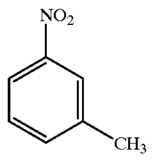

NAS-5

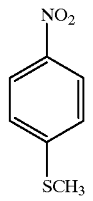

-continued

NAS-6

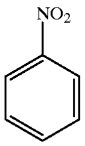

NAS-7

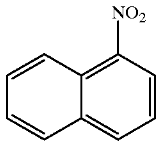

NAS-8

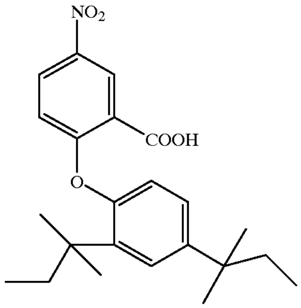

NAS-9

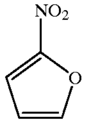

NAS-10

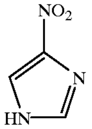

NAS-11

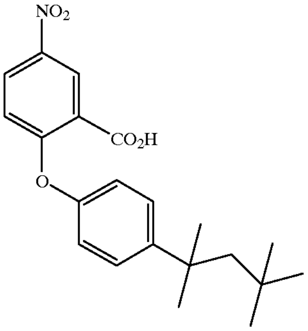

NAS-12

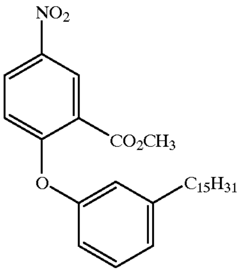

-continued

NAS-13

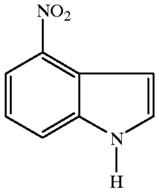

NAS-14

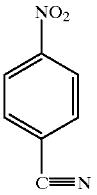

NAS-15

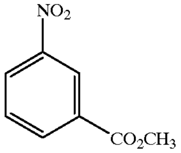

or

NAS-16

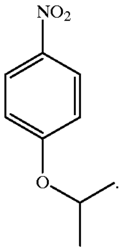

6. The method of claim 1 wherein $R_1$ is an alkyl, aryl, amido, alkoxy or aryloxy group, $R_2$ is an alkyl or aryl group, X is hydrogen, halo, or an alkylthiol, arylthiol or phenoxy group, and Y is halo, or an aryloxy, acyloxy or alkoxy group.

7. The method of claim 6 wherein $R_1$ is an alkyl, phenyl or phenoxy group, $R_2$ is a phenyl or alkyl group, X is hydrogen, chloro, phenoxy or carboethoxyethylthio, and Y is halo, or a p-nitrophenoxy or acetoxy group.

8. The method of claim 1 wherein said formate salt is present in an amount of from about 3 to about 6 molar equivalents based on the concentration of the compound of Structure IV.

9. The method of claim 1 wherein said reaction medium comprises water, ethyl acetate, propyl acetate, isopropanol, tetrahydrofuran, acetonitrile, or a mixture of any two or more of these solvents.

10. The method of claim 1 wherein the compound of Structure IV is

CP-1

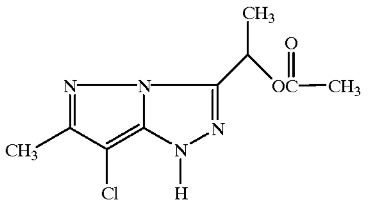

-continued
CP-2
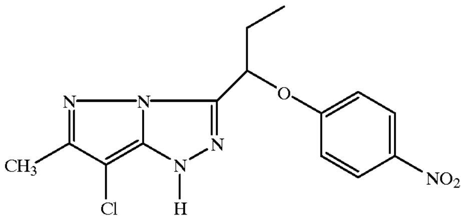
CP-3
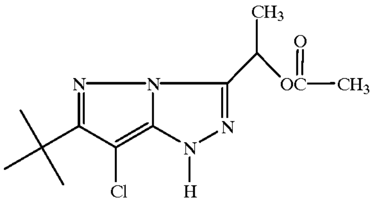
CP-4
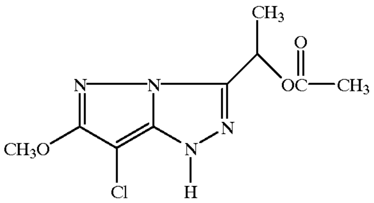
CP-5
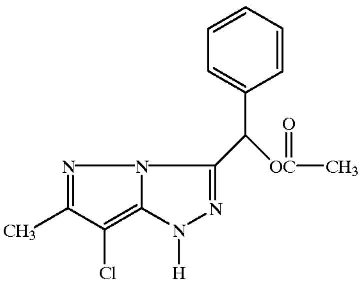
CP-6
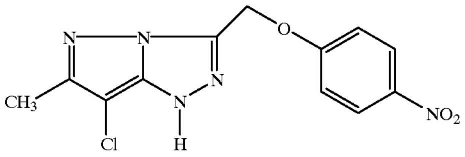
CP-7
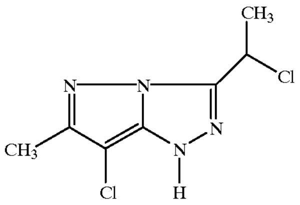
-continued
CP-8
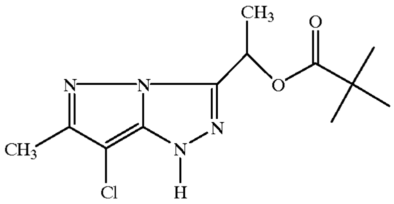
CP-9
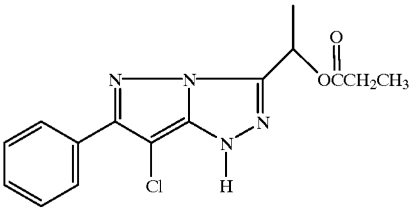
CP-10
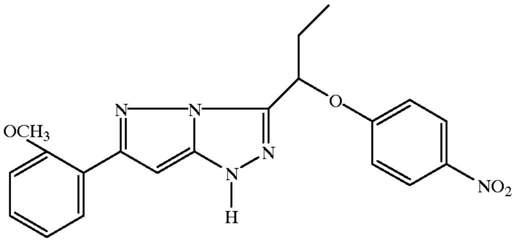
CP-11
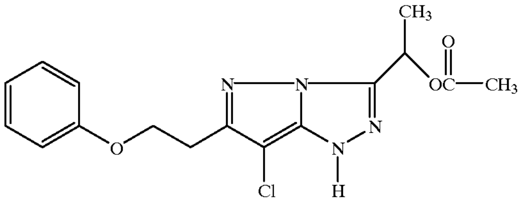
CP-12
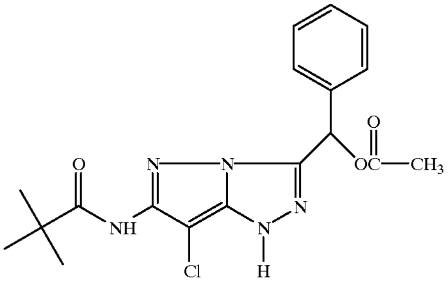

-continued
CP-13
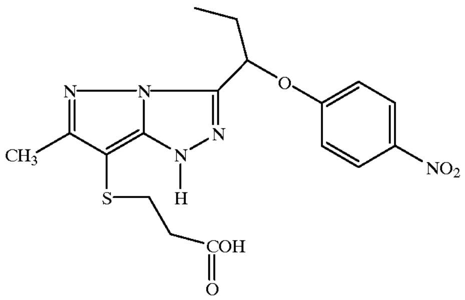
CP-14
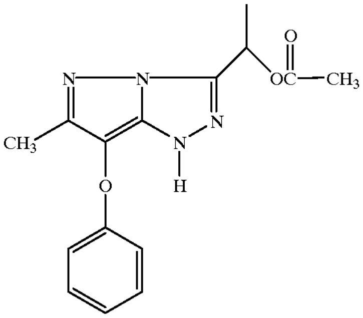
CP-15
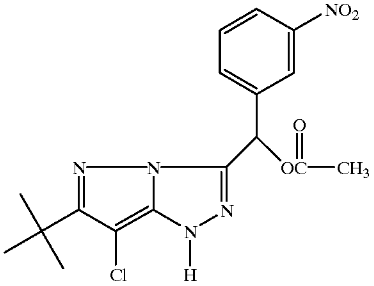
-continued
CP-16
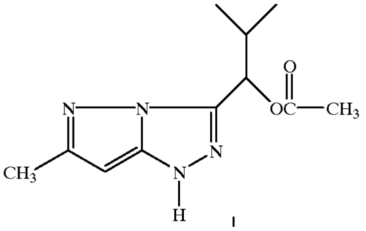
CP-17
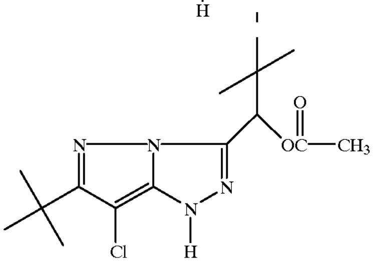
or
CP-18
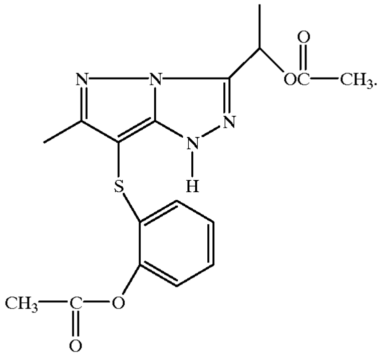
* * * * *